US012636450B1

(12) United States Patent      (10) Patent No.:    US 12,636,450 B1

Matthews                     (45) Date of Patent:      May 26, 2026

(54) TRACHEAL BIB

(71) Applicant: Clair Matthews, Tuscaloosa, AL (US)

(72) Inventor: Clair Matthews, Tuscaloosa, AL (US)

( * ) Notice: Subject to any disclaimer, the term of this patent is extended or adjusted under 35 U.S.C. 154(b) by 712 days.

(21) Appl. No.: 18/080,028

(22) Filed: Dec. 13, 2022

(51) Int. Cl.
     A61M 16/04        (2006.01)

(52) U.S. Cl.
     CPC ...... A61M 16/047 (2013.01); A61M 16/0497 (2013.01)

(58) Field of Classification Search
     CPC ..................... A61M 16/047; A61M 16/0497
     See application file for complete search history.

(56)             References Cited

U.S. PATENT DOCUMENTS

| | | | | | |
|---|---|---|---|---|---|
| 3,286,713 | A | * | 11/1966 | Kurtz | ................ A61F 13/01021 |
| | | | | | 128/207.14 |
| 3,585,997 | A | * | 6/1971 | Ancerewicz, Jr. | .. A61M 16/047 |
| | | | | | 604/338 |
| 4,463,757 | A | | 8/1984 | Schmidt | |
| 4,891,846 | A | * | 1/1990 | Sager | ................. A41D 13/1245 |
| | | | | | 2/48 |
| 5,058,579 | A | * | 10/1991 | Terry | ................. A61M 16/047 |
| | | | | | 128/207.14 |
| 5,101,822 | A | * | 4/1992 | Kimmel | ................ A61M 25/02 |
| | | | | | 128/207.14 |
| 5,368,023 | A | * | 11/1994 | Wolf | ..................... A61M 25/02 |
| | | | | | 604/179 |
| 5,485,837 | A | * | 1/1996 | Solesbee | ........... A61M 16/0465 |
| | | | | | 128/207.14 |
| 5,529,062 | A | * | 6/1996 | Byrd | ...................... A61M 25/02 |
| | | | | | 128/207.14 |
| 8,074,650 | B2 | * | 12/2011 | Steeves | ............... A61M 16/047 |
| | | | | | 128/207.14 |
| D978,484 | S | * | 2/2023 | Schiffres | ........................ D2/861 |
| 2009/0145439 | A1 | * | 6/2009 | Peichel | ............. A61M 16/0488 |
| | | | | | 128/207.17 |
| 2009/0211573 | A1 | * | 8/2009 | Russo | ............... A61M 16/0488 |
| | | | | | 128/207.14 |
| 2012/0047617 | A1 | * | 3/2012 | Didiodato | ........... A61M 16/047 |
| | | | | | 2/48 |
| 2016/0256647 | A1 | * | 9/2016 | Thomas | .............. A61M 16/047 |
| 2020/0108217 | A1 | * | 4/2020 | Vickers | ............. A61M 16/0497 |

FOREIGN PATENT DOCUMENTS

| | | | | | |
|---|---|---|---|---|---|
| CN | 208492907 | U | * | 2/2019 | |
| CN | 110840656 | A | * | 2/2020 | ............. D04H 1/425 |
| CN | 210096622 | U | * | 2/2020 | |

(Continued)

*Primary Examiner* — Kathryn E Ditmer

(74) *Attorney, Agent, or Firm* — Sanchelima & Associates, P.A.; Christian Sanchelima; Jesus Sanchelima

(57)            ABSTRACT

A tracheal bibb including a tie assembly with an absorption assembly and a tube assembly. Tie assembly includes a tracheal tie having a band that goes around the neck and can be adjusted. Tracheal tie includes in an inner surface an inner layer, wherein has a comfortable material for the user's neck. The inner layer includes a ventilation portion that prevents neck sweating. Absorption assembly includes a deeper tracheal sponge that is attachable to the tracheal tie placed around the tube assembly and between the neck and the tracheal tie. Deeper tracheal sponge has a curved shape that permits to absorb secretions more efficiently from the user's tracheostomy.

2 Claims, 3 Drawing Sheets

(56)         References Cited

FOREIGN PATENT DOCUMENTS

| | | | | | |
|---|---|---|---|---|---|
| DE | 20106113 | U1 | * | 6/2001 | .......... A61M 16/047 |
| DE | 202004005449 | U1 | * | 7/2004 | ........ A61M 16/0488 |
| DE | 102005003350 | A1 | * | 8/2006 | .......... A61M 16/047 |
| DE | 102006056946 | A1 | * | 6/2008 | .......... A61M 16/047 |
| DE | 202013004245 | U1 | * | 6/2013 | ........ A61M 16/0497 |
| ES | 2686833 | A1 | * | 10/2018 | .......... A61M 16/047 |
| TW | M544334 | U | * | 7/2017 | |

* cited by examiner

10

TRACHEAL BIB

1. FIELD OF THE INVENTION

The present invention relates to a tracheostomy bib and, more particularly, to a tracheal bib that is capable of being attached to a tracheal tie, thereby enhancing secretion absorption from the tracheostomy.

2. DESCRIPTION OF THE RELATED ART

Several designs for tracheostomy bibs have been designed in the past. None of them, however, include a deeper tracheal sponge attachable to a tracheostomy tie that has a curved shape permitting a more efficient secretion absorption.

Applicant believes that a related reference corresponds to U.S. Pat. No. 4,463,757 issued for covering device for tracheostomy stoma. Applicant believes that another related reference corresponds to U.S. Pat. No. 3,286,713 issued for surgical dressing. None of these references, however, teach of a tracheostomy dressing comprising an absorbent collar and bib for use with a tracheostomy.

Other documents describing the closest subject matter provide for a number of more or less complicated features that fail to solve the problem in an efficient and economical way. None of these patents suggest the novel features of the present invention.

III. SUMMARY OF THE INVENTION

It is one of the objects of the present invention to provide an improved means to stabilize tracheostomy tubes.

It is another object of this invention to facilitate proper air flow between the skin and the tracheal tie.

It is still another object of the present invention to protect the skin from secretions.

It is yet another object of this invention to provide such a device that is inexpensive to implement and maintain while retaining its effectiveness.

Further objects of the invention will be brought out in the following part of the specification, wherein detailed description is for the purpose of fully disclosing the invention without placing limitations thereon.

IV. BRIEF DESCRIPTION OF THE DRAWINGS

With the above and other related objects in view, the invention consists in the details of construction and combination of parts as will be more fully understood from the following description, when read in conjunction with the accompanying drawings in which.

Figure 3:
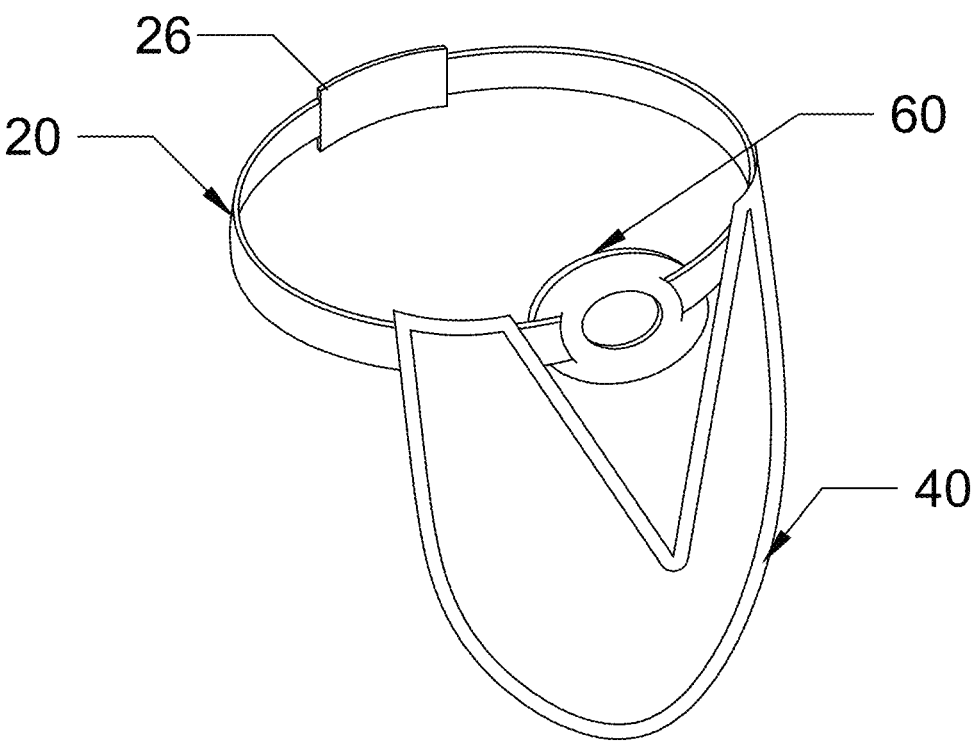

FIG. 3 illustrates a front perspective view of the present invention 10, wherein the tracheostomy tube 62 goes through the flange of the tracheal tie 22.

Figure 4:
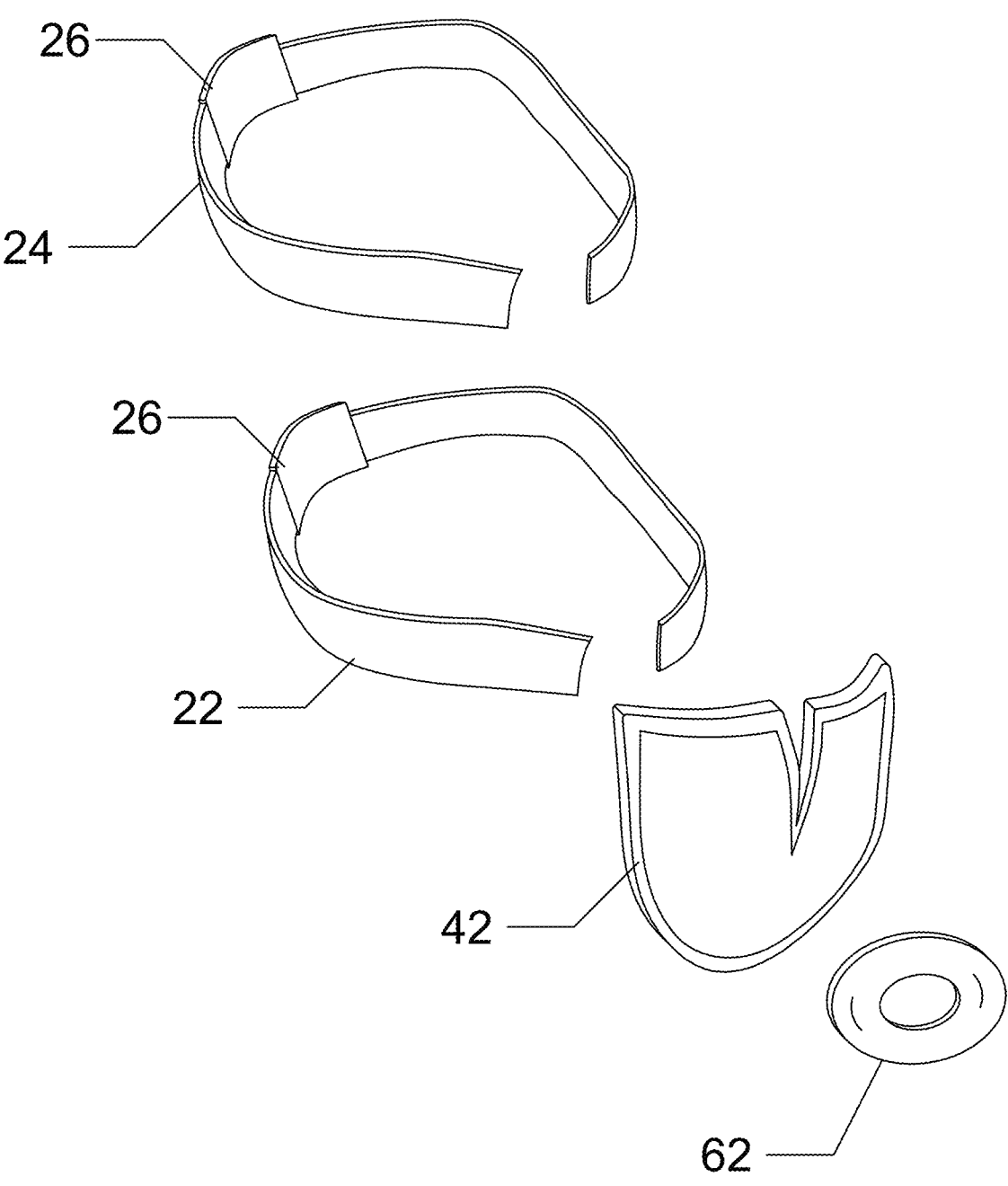

FIG. 4 is a representation of an exploded view of the elements of the present invention 10 showing the assembling therebetween, wherein the inner layer 24 is placed in an internal surface of the tracheal tie 22, the deeper tracheal sponge 42 is attached to a front portion of tracheal tie 22, and the tracheostomy tube that goes through the flange.

V. DETAILED DESCRIPTION OF THE EMBODIMENTS OF THE INVENTION

Referring now to the drawings, where the present invention is generally referred to with numeral 10, it can be observed that it basically includes a tie assembly 20, an absorption assembly 40 and a tube assembly 60. It should be understood there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

Figure 2:
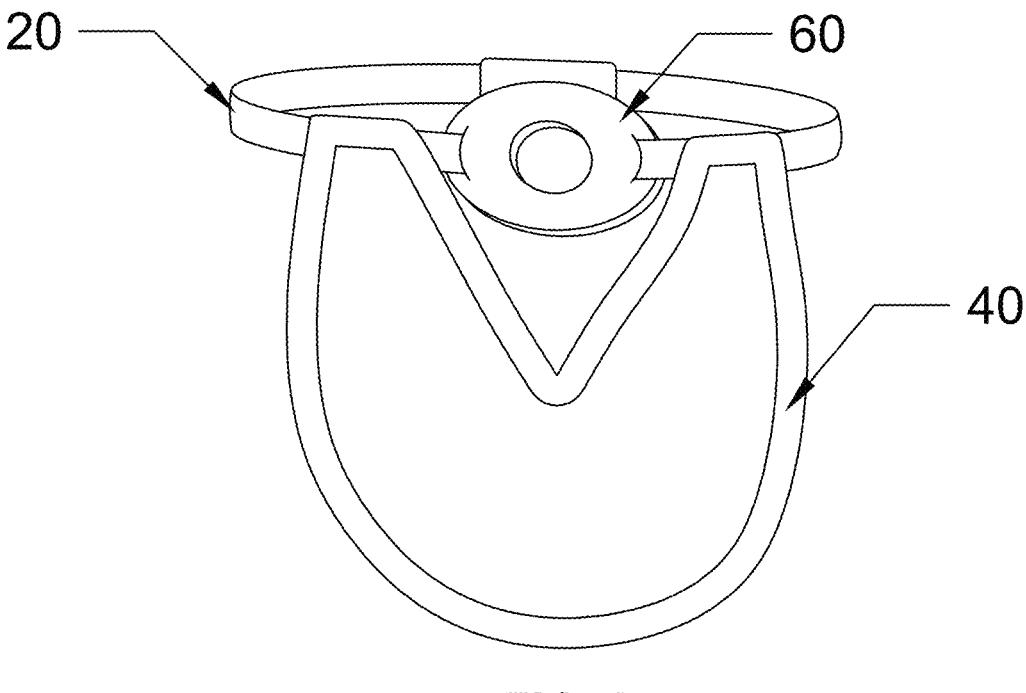
FIG. 2 shows an isometric view of the present invention 10, wherein the inner layer has a ventilation portion.

Tie assembly 20 includes a tracheal tie 22, an inner layer 24 and ventilation portion 26. In an exemplary embodiment, tracheal tie 22 may consist of a band and a flange, wherein the band goes around a user's neck. The tracheal tie 22 may be made of natural fibers, Nonetheless, other materials like synthetic fibers or any other material known in the art may be suitable. In a suitable embodiment, tracheal tie 22 includes in a portion of the edges thereof a hook and loop fastener, wherein said portions may be folded back to be attached to a portion of the body of the tracheal tie 22. Nevertheless, it should be considered for the tracheal tie 22 that other fasteners known in the art may be suitable. In preferred embodiment, the flange of the tracheal tie 22 may include two openings placed proximal to the edges thereof, wherein the openings may have a suitable area so a portion of the edges of the band may pass through thereof. A portion of the edges of the band when have passed through the openings, can be folded back and to be attached to the body of the tracheal tie 22 by means of the hook and loop fastener, thereby the tracheal tie 22 may be adjusted to the user's neck. In a suitable embodiment, inner layer 24 may be a band with a rectangular shape, wherein the inner layer 24 may be placed in a portion of an internal surface of the tracheal tie 22. Nevertheless, it should be considered that inner layer 24 may have an oval shape, a regular shape, an irregular shape, or any other variation thereof. In one embodiment, inner layer 24 may be made of cotton fibers, synthetic fibers, or any other suitable material. In a preferred embodiment, inner layer 24 may be placed symmetrically parallel to the band of the tracheal tie 22. Best depicted in FIG. 2. Nonetheless, it should be considered that the area of the inner layer 24 may be bigger than the band of the tracheal tie 22. In a suitable embodiment, tracheal tie 22 and inner layer 24 may include ventilation portion 26, wherein the ventilation portion 26 may be placed in a portion of the body of the tracheal tie 22 and the inner layer 24. As shown in FIG. 4. In one embodiment, ventilation portion 26 may have a suitable area, allowing the external air to pass through thereof preventing the covered skin from the user's neck by the tracheal tie 22 increasing its temperature.

Figure 1:
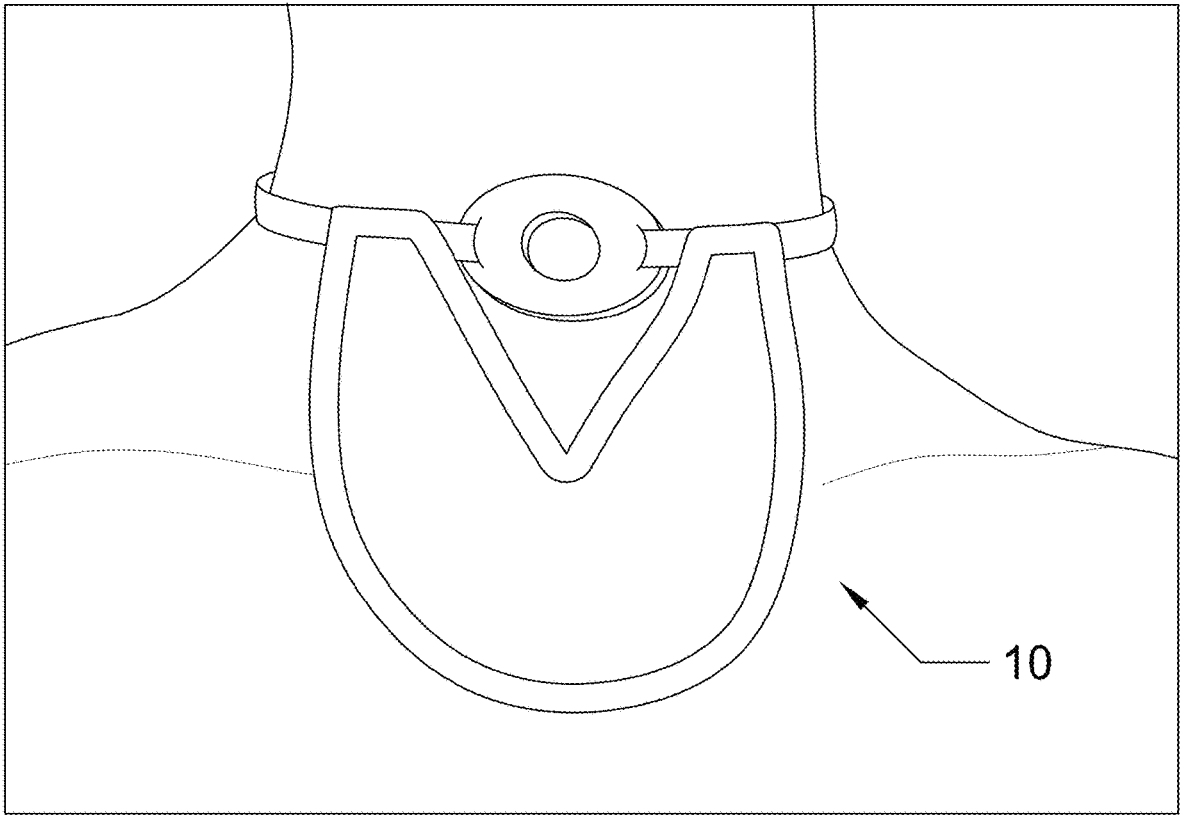
FIG. 1 represents an operational view of an exemplary embodiment of the present invention 10.

Absorption assembly 40 may include a deeper tracheal sponge 42. In a suitable embodiment deeper tracheal sponge 42 may have an irregular shape, wherein in the base may have a triangular shape with a rounded peak oriented toward down in a longitudinal position. In a top portion, deeper tracheal sponge 42 may have a V-cut from the uppermost portion to a central portion thereof. In a preferred embodiment, deeper tracheal sponge 42 may be made of polyester, polyurethane, vegetal cellulose, or any other suitable material for sponges. Nonetheless, it should be considered for deeper tracheal sponge 42 may be made of any other absorbent material suitable for human skin. Deeper tracheal sponge 42 may be configured to be in contact with the skin of the user's neck, wherein a top portion of the deeper tracheal sponge 42 may be attached to the tracheal tie 22, thereby deeper tracheal sponge 42 may absorb the secretions emitted from the stoma and the V-cut may have a suitable length where the flange may be placed between the attached portion of the deeper tracheal sponge 42. As best depicted in FIG. 1.

Tube assembly 60 may include a tracheostomy tube 62, wherein a portion of the tracheostomy tube 62 pass through an opening included in the flange and the opening of the deeper tracheal sponge 42 until the stoma, another portion of the tracheostomy tube 62 extends past from the flange so the oxygen can pass through thereof. Best depicted in FIG. 1.

FIG. 3 illustrates the assembly between the tie assembly 20, the absorption assembly 40 and the tube assembly 60, wherein the tie assembly 20 surrounds the neck of the user and may be adjusted by means of the hook and loop fastener. In a preferred embodiment absorption assembly 40 may be placed between the skin and the flange, wherein the deeper tracheal sponge 42 may absorb any secretion produced from the stoma. The deeper tracheal sponge 42 may be replaced by detaching the hook and loop fastener of at least one side of the band so the flange does not press the deeper tracheal sponge against the skin 42, thereby the deeper tracheal sponge 42 may be removed by sliding it down by means of the triangular cut and a new deeper tracheal sponge 42 may be paced by sliding it up permitting the user to have a clean area around the stoma.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A tracheal bib, comprising:

a tracheal tie having an elongated rectangular shape with a width, and a ventilation portion placed in a central portion of the tracheal tie, said ventilation portion has a rectangular body with a width greater than that of the tracheal tie; wherein an coextensive inner layer is attached to an inner surface of the tracheal tie, thereby defining a lining;

a tracheal sponge comprising: an upper portion having a V-shaped cut extending downward from an uppermost edge thereof wherein said V-shaped cut defines two upwardly-extending arms and a slot therebetween, and a lower portion with a U-shaped base;

wherein said two upwardly-extending arms are attached to said tracheal tie;

a flange having a body with a central opening and lateral openings;

wherein distal ends of the tracheal tie are attachable to the lateral openings of the flange;

wherein, when attached to the tracheal tie, the flange is configured to be located in the slot formed by the two upwardly-extending arms.

2. A tracheal bib, consisting of:

a tracheal tie having an elongated rectangular body with a width and distal ends having hook-and-loop fasteners thereon, and a ventilation portion placed in a central portion of the tracheal tie, said ventilation portion has a rectangular body with a width greater than that of the tracheal tie; wherein a coextensive inner layer made of cotton is attached to an inner surface of the tracheal tie, thereby defining a cotton lining;

a tracheal sponge formed by an upper portion having a V-shaped cut extending downward from an uppermost edge thereof wherein said V-shaped cut defines two upwardly-extending arms and a slot therebetween, and a lower portion with a U-shaped base;

wherein said two upwardly-extending arms are attached to said tracheal tie;

a flange having a body with a central opening and lateral openings;

wherein the distal ends of the tracheal tie are attachable to the lateral openings of the flange;

wherein, when attached to the tracheal tie, the flange is configured to be located in the slot formed by the two upwardly-extending arms;

wherein, when assembled, the ventilation portion is at an opposite side of the tracheal tie relative to said flange.

* * * * *